(12) United States Patent
Fisher

(10) Patent No.: US 9,292,938 B2
(45) Date of Patent: *Mar. 22, 2016

(54) METHODS AND SYSTEMS FOR IMAGE DATA PROCESSING

(71) Applicant: Luminex Corporation, Austin, TX (US)

(72) Inventor: Matthew S. Fisher, Austin, TX (US)

(73) Assignee: Luminex Corporation, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/743,927

(22) Filed: Jun. 18, 2015

(65) Prior Publication Data

US 2015/0287212 A1  Oct. 8, 2015

Related U.S. Application Data

(63) Continuation of application No. 14/512,780, filed on Oct. 13, 2014, now Pat. No. 9,063,088, which is a continuation of application No. 13/653,789, filed on Oct. 17, 2012, now Pat. No. 8,859,996.

(60) Provisional application No. 61/627,851, filed on Oct. 18, 2011.

(51) Int. Cl.
 *G01N 21/64* (2006.01)
 *G06T 7/20* (2006.01)
 (Continued)

(52) U.S. Cl.
 CPC ............... *G06T 7/206* (2013.01); *G01N 15/14* (2013.01); *G01N 21/64* (2013.01); *G01P 5/20* (2013.01);
 (Continued)

(58) Field of Classification Search
 CPC ...... G02B 21/16; G02B 21/367; G02B 21/06; G02B 21/008; G02B 7/38; G01N 21/6458; G01N 2021/6421; G01N 2021/6419; G01N 15/1463; G01N 15/1475
 USPC ....................................................... 250/459.1
 See application file for complete search history.

(56) References Cited

U.S. PATENT DOCUMENTS 5,107,422 A   4/1992   Kamentsky et al.
5,162,990 A   11/1992   Odeyale et al.
(Continued)

FOREIGN PATENT DOCUMENTS

CN   1556497   12/2004
EP   0421736   4/1991
(Continued)

OTHER PUBLICATIONS

Office Action in India Application No. 359/MUMNP/2008 dated Jul. 25, 2013, 4 pages.
(Continued)

*Primary Examiner* — Marcus Taningco
(74) *Attorney, Agent, or Firm* — Meyertons, Hood, Kivlin, Kowert & Goetzel, P.C.

(57) ABSTRACT

Embodiments of the computer-implemented methods, storage mediums, and systems may be configured to determine locations of particles within a first image of the particles. The particles may have fluorescence-material associated therewith. The embodiments may include calculating a transform parameter, and the transform parameter may define an estimated movement in the locations of the particles between the first image of the particles and a second image of the particles. The embodiments may further including applying the transform parameter to the locations of the particles within the first image to determine movement locations of the particles within the second image.

24 Claims, 6 Drawing Sheets

(51) Int. Cl.
  *G01P 5/20* (2006.01)
  *G01N 15/14* (2006.01)
  *G06T 7/00* (2006.01)
  *G06T 3/00* (2006.01)

(52) U.S. Cl.
  CPC ............ *G06T 3/0068* (2013.01); *G06T 7/0012* (2013.01); *G01N 2021/6497* (2013.01); *G06T 2207/10064* (2013.01)

(56) References Cited

U.S. PATENT DOCUMENTS

| | | | |
|---|---|---|---|
| 5,206,699 | A | 4/1993 | Stewart et al. |
| 5,337,081 | A | 8/1994 | Kamiya et al. |
| 5,579,409 | A | 11/1996 | Vaidyanathan et al. |
| 5,623,560 | A | 4/1997 | Nakajima et al. |
| 5,715,334 | A | 2/1998 | Peters |
| 5,736,330 | A | 4/1998 | Fulton |
| 5,751,839 | A | 5/1998 | Drocourt et al. |
| 5,828,766 | A | 10/1998 | Gallo |
| 5,836,872 | A | 11/1998 | Kenet et al. |
| 5,841,148 | A | 11/1998 | Some et al. |
| 5,981,180 | A | 11/1999 | Chandler et al. |
| 6,057,107 | A | 5/2000 | Fulton |
| 6,165,734 | A | 12/2000 | Garini et al. |
| 6,268,222 | B1 | 7/2001 | Chandler et al. |
| 6,284,465 | B1 | 9/2001 | Wolber |
| 6,307,959 | B1 | 10/2001 | Mandelbaum et al. |
| 6,449,562 | B1 | 9/2002 | Chandler et al. |
| 6,514,295 | B1 | 2/2003 | Chandler et al. |
| 6,524,793 | B1 | 2/2003 | Chandler et al. |
| 6,528,165 | B2 | 3/2003 | Chandler |
| 6,548,257 | B2 | 4/2003 | Lockhart et al. |
| 6,592,822 | B1 | 7/2003 | Chandler |
| 6,611,767 | B1 | 8/2003 | Fiekowsky et al. |
| 6,649,414 | B1 | 11/2003 | Chandler et al. |
| 6,687,395 | B1 | 2/2004 | Dietz et al. |
| 6,713,264 | B2 | 3/2004 | Luttermann et al. |
| 6,730,521 | B1 | 5/2004 | Cassells |
| 6,763,149 | B2 | 7/2004 | Riley et al. |
| 6,806,052 | B2 | 10/2004 | Bridgham et al. |
| 6,806,954 | B2 | 10/2004 | Sandstrom |
| 6,829,376 | B2 | 12/2004 | Bartell |
| 6,876,760 | B1 | 4/2005 | Vaisberg et al. |
| 6,885,440 | B2 | 4/2005 | Silcott et al. |
| 6,903,207 | B2 | 6/2005 | Mirkin et al. |
| 6,939,720 | B2 | 9/2005 | Chandler et al. |
| 7,236,620 | B1 | 6/2007 | Gurcan |
| 8,031,918 | B2 | 10/2011 | Roth |
| 2001/0041347 | A1 | 11/2001 | Sammak et al. |
| 2002/0141631 | A1 | 10/2002 | Vaisberg et al. |
| 2002/0164063 | A1 | 11/2002 | Heckman |
| 2002/0176606 | A1 | 11/2002 | Wernet et al. |
| 2003/0016860 | A1 | 1/2003 | Sugawara |
| 2003/0036067 | A1 | 2/2003 | Schwartz |
| 2003/0096322 | A1 | 5/2003 | Giuliano et al. |
| 2003/0138140 | A1 | 7/2003 | Marcelpoil et al. |
| 2004/0071328 | A1 | 4/2004 | Vaisberg |
| 2004/0095611 | A1 | 5/2004 | Watanabe et al. |
| 2005/0009032 | A1 | 1/2005 | Coleman et al. |
| 2005/0078881 | A1 | 4/2005 | Xu et al. |
| 2006/0014137 | A1 | 1/2006 | Ghosh et al. |
| 2006/0105395 | A1 | 5/2006 | Pempsell |
| 2007/0064990 | A1 | 3/2007 | Roth |
| 2008/0111086 | A1 | 5/2008 | Betzig et al. |
| 2011/0045993 | A1 | 2/2011 | Kent et al. |
| 2011/0316998 | A1 | 12/2011 | Kishima |

FOREIGN PATENT DOCUMENTS

| | | |
|---|---|---|
| EP | 1439384 | 7/2004 |
| EP | 2194506 | 6/2010 |
| JP | 7-264483 | 10/1995 |
| JP | 8-304288 | 11/1996 |
| JP | 2000299874 | 10/2000 |
| JP | 2002344978 | 11/2002 |
| JP | 2003262588 | 9/2003 |
| JP | 2005127790 | 5/2005 |
| JP | 2005527827 | 9/2005 |
| WO | 00/29984 | 5/2000 |
| WO | 01/11340 | 2/2001 |
| WO | 03/069421 | 8/2003 |
| WO | 03100474 | 12/2003 |
| WO | 2004036162 | 4/2004 |
| WO | 2004-055505 | 7/2004 |
| WO | 2005001436 | 1/2005 |

OTHER PUBLICATIONS

Office Action in Japanese Patent Application No. 2012-000148 issued Dec. 3, 2013, 4 pages.
Office Action in Japanese Patent Application No. 2012-000148 issued Jan. 4, 2013, 6 pages.
Office Action in Chinese Application No. 201210021093.7 dated Dec. 11, 2013, 12 pages.
Office Action in Korean Patent Application No. 10-2008-7009141 dated Aug. 20, 2012, 7 pages.
Office Action in Chinese Patent Application No. 200680034792.8 dated Sep. 26, 2011, 5 pages.
Office Action in Japanese Patent Application No. 2008-532362 dated Oct. 4, 2011, 3 pages.
Office Communication in European Patent Application No. 06 803 948.6 dated Jan. 21, 2011, 6 pages.
International Search Report in Application No. PCT/US2006/036733 mailed Aug. 20, 2007, 6 pages.
Statistical Algorithms Description Document, Affymetrix, Inc., 2002, pp. 1-28.
Extended European Search Report Patent Application No. 10183403.4 dated Aug. 25, 2011, 7 pages.
International Search Report and Written Opinion in PCT Application No. PCT/US2012/060639 mailed Mar. 29, 2013, 10 pages.
Office Action in Canadian Application No. 2,623,130 mailed May 15, 2014, 3 pages.
Second Office Action in Chinese Application No. 201210021093.7 mailed Jul. 21, 2014, 10 pages.
European Search Report in Application No. 12842618.6 mailed Jan. 9, 2015, 5 pages.

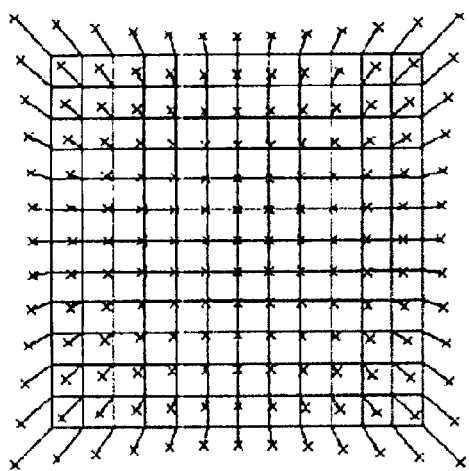
FIG. 3A - CL
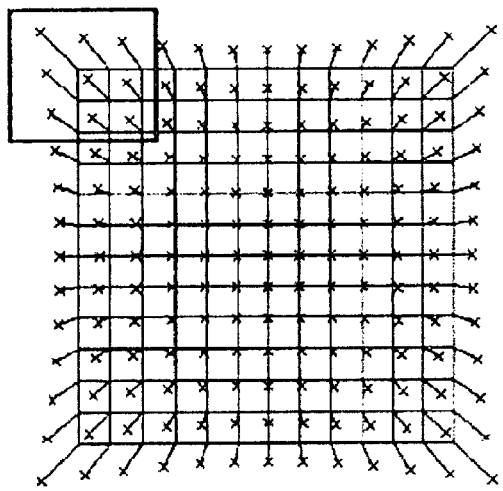
FIG. 3B - RP
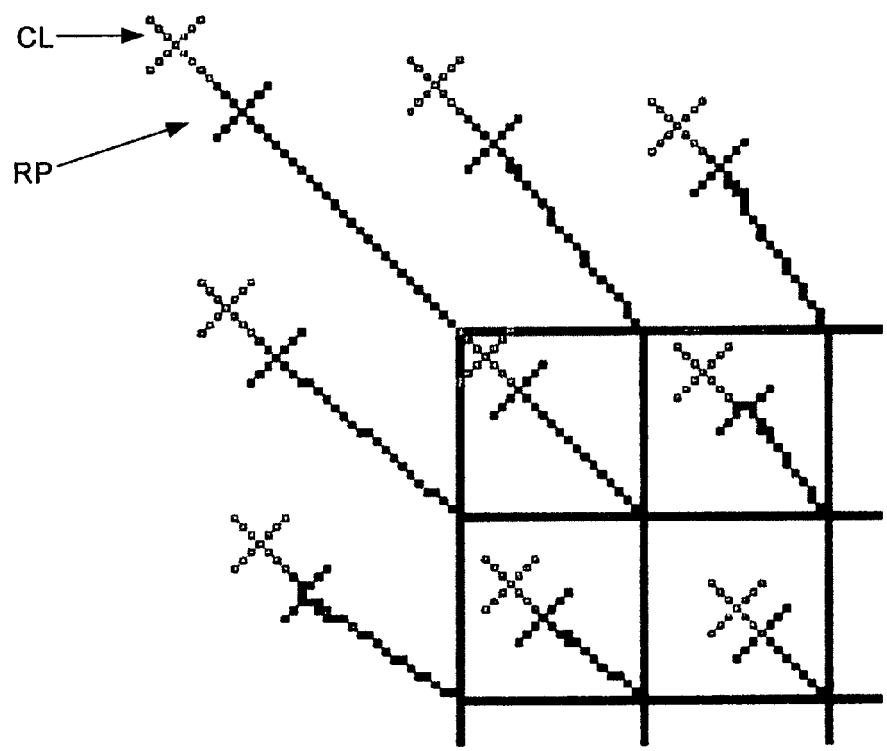
FIG. 3C - difference

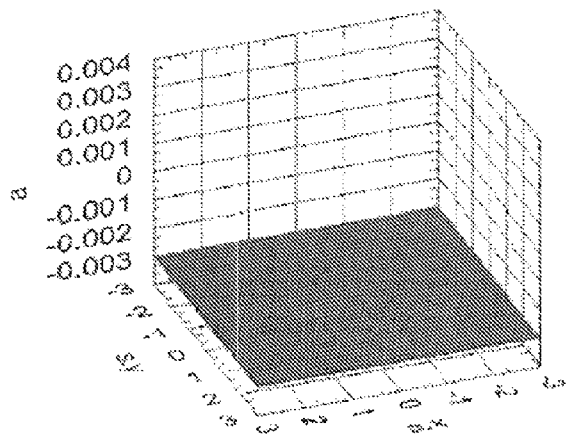
FIG. 6A - a = -.0030
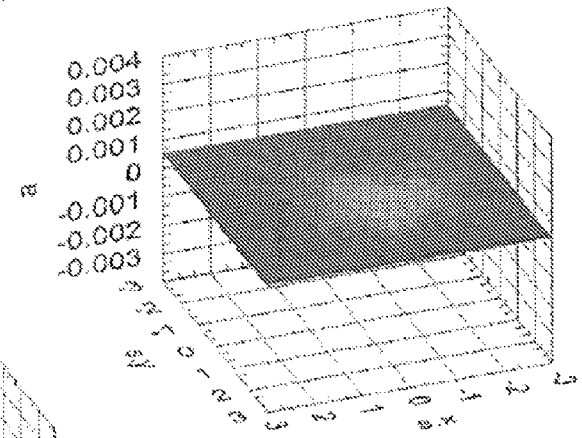
FIG. 6B - a = .0005
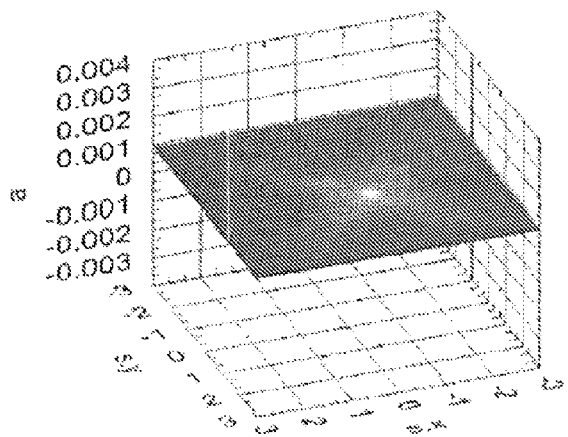
FIG. 6C - a = .0009
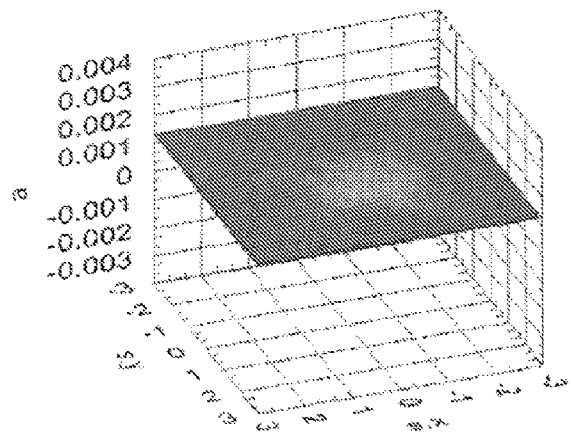
FIG. 6D - a = .0013

METHODS AND SYSTEMS FOR IMAGE DATA PROCESSING

PRIORITY CLAIM

The present application is a continuation of U.S. application Ser. No. 14/512,780, filed Oct. 13, 2014, which is a continuation of U.S. application Ser. No. 13/653,789, filed Oct. 17, 2012 (now U.S. Pat. No. 8,859,996), which claims priority to U.S. Provisional Appl. No. 61/627,851, filed Oct. 18, 2011; the disclosures of each of the above-referenced applications are incorporated by reference herein in their entireties.

BACKGROUND OF THE INVENTION

1. Field of the Invention

This invention generally relates to methods and systems for image data processing. Certain embodiments relate to methods and systems for performing one or more steps for processing multiple images of particles to account for movement of the particles between the images.

2. Description of the Related Art

The following descriptions and examples are not admitted to be prior art by virtue of their inclusion within this section.

Imaging using detectors such as charged coupled device (CCD) detectors is employed in several currently available instruments in biotechnology applications. Such applications may require taking multiple images of particles. In these multiple images of the particles, the particles may appear to move. In images of particles taken close together in time (or perhaps at the same time), the particles may appear to shift or move. Accordingly, it would be desirable to develop methods and systems for data processing of images of particles to account for movement of particles between images.

SUMMARY OF THE INVENTION

The problem outlined above may be in large part addressed by computer-implemented methods, storage mediums, and systems for performing one or more steps associated with data image processing of particles. The following are mere exemplary embodiments of the computer-implemented methods, storage mediums, and systems and are not to be construed in any way to limit the subject matter of the claims.

Embodiments of the computer-implemented methods, storage mediums, and systems may be configured to determine locations of particles within a first image of the particles, wherein the particles have fluorescence-material associated therewith; calculate a transform parameter, wherein the transform parameter defines an estimated movement in the locations of the particles between the first image of the particles and a second image of the particles; and apply the transform parameter to the locations of the particles within the first image to determine movement locations of the particles within the second image.

In some embodiments of the methods, storage mediums, and systems, the transform parameter includes a radial component and a constant component. The radial component may be proportional to a distance between the locations of particles within the first image and a center of the first image.

In some embodiments of the methods, storage mediums, and systems, calculating the transform parameter may include estimating estimated locations of particles within the second image and calculating potential transform parameters based on the locations of the particles within the first image and the estimated locations of the particles in the second image. In some embodiments, calculating the transform parameter may further include determining an optimal transform parameter based on the potential transform parameters.

In some embodiments of the methods, storage mediums, and systems, estimating the estimated locations of the particles within the second image may include determining maximal integral locations based on the second image and the locations of the particles within the first image. Moreover, in some embodiments, determining the optimal transform parameter comprises using a Hough transform.

Some embodiments of the methods, storage mediums, and systems, may further include calculating an error component based on a force between the particles.

The terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A-C illustrate potential grid distortion between a first image of particles and a second image of particles;

FIGS. 6A-6D illustrate a vote space used in determining an optimal transform parameter.

DETAILED DESCRIPTION

Figure 1:
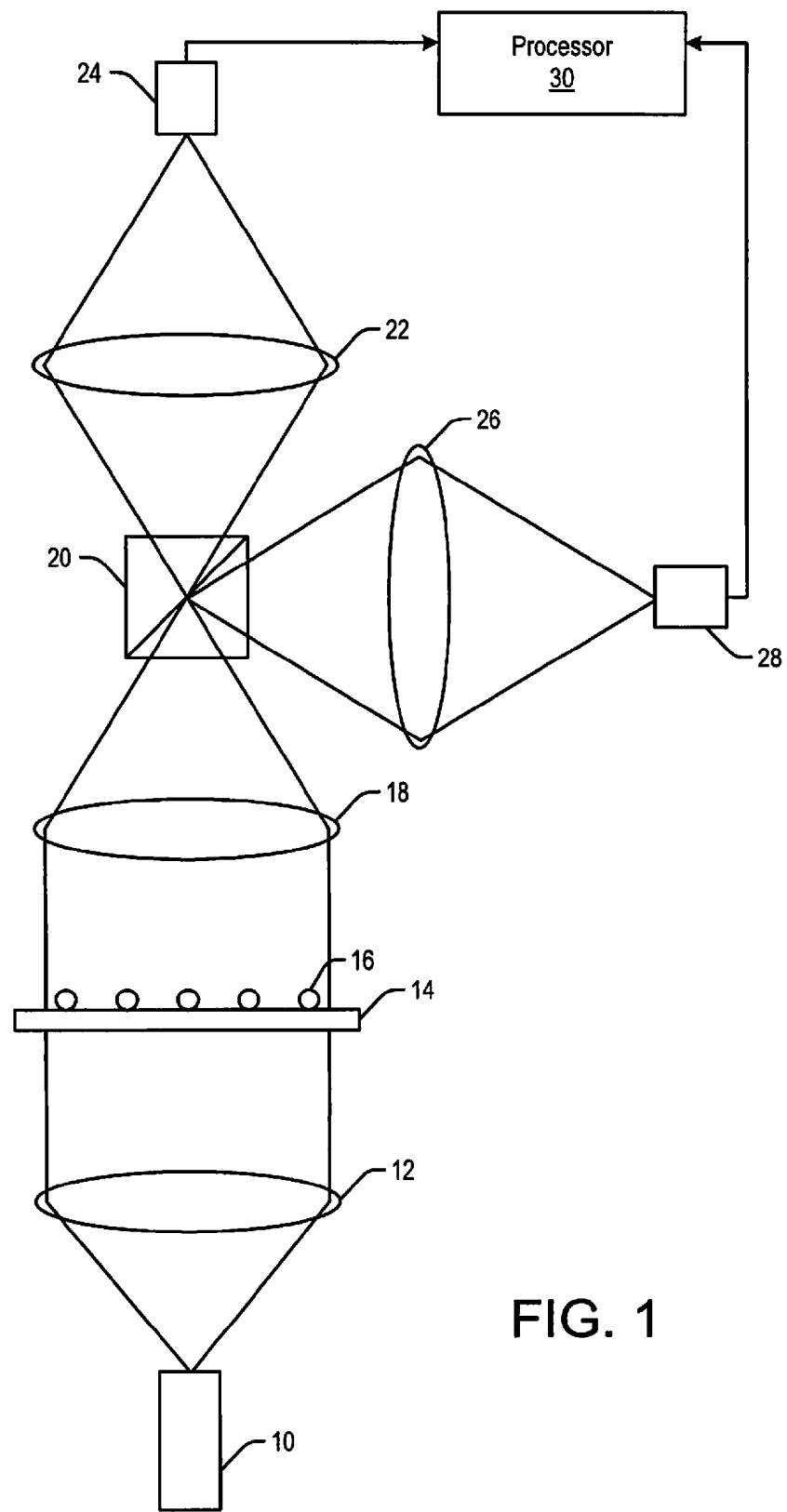
FIG. 1 is a schematic diagram illustrating a cross-sectional view of one embodiment of a system configured to acquire and process images of particles.

Although embodiments are described herein with respect to particles, it is to be understood that the systems and methods described herein may also be used with microspheres, polystyrene beads, microparticles, gold nanoparticles, quantum dots, nanodots, nanoparticles, nanoshells, beads, microbeads, latex particles, latex beads, fluorescent beads, fluorescent particles, colored particles, colored beads, tissue, cells, micro-organisms, organic matter, non-organic matter, or any other discrete substances known in the art. The particles may serve as vehicles for molecular reactions. Examples of appropriate particles are illustrated and described in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference as if fully set forth herein. The systems and methods described herein may be used with any of the particles described in these patents. In addition, particles for use in method and system embodiments described herein may be obtained from manufacturers such as Luminex Corporation of Austin, Tex. The terms "particles" and "microspheres" and "beads" are used interchangeably herein.

In addition, the types of particles that are compatible with the systems and methods described herein include particles with fluorescent materials attached to, or associated with, the surface of the particles. These types of particles, in which fluorescent dyes or fluorescent particles are coupled directly to the surface of the particles in order to provide the classification fluorescence (i.e., fluorescence emission measured and used for determining an identity of a particle or the subset to which a particle belongs), are illustrated and described in U.S. Pat. No. 6,268,222 to Chandler et al. and U.S. Pat. No. 6,649,414 to Chandler et al., which are incorporated by reference as if fully set forth herein. The types of particles that can be used in the methods and systems described herein also include particles having one or more fluorochromes or fluorescent dyes incorporated into the core of the particles.

Particles that can be used in the methods and systems described herein further include particles that in of themselves will exhibit one or more fluorescent signals upon exposure to one or more appropriate light sources. Furthermore, particles may be manufactured such that upon excitation the particles exhibit multiple fluorescent signals, each of which may be used separately or in combination to determine an identity of the particles. As described below, image data processing may include classification of the particles, particularly for a multi-analyte fluid, as well as a determination of the amount of analyte bound to the particles. Since a reporter signal, which may represent the amount of analyte bound to the particle, is typically unknown during operations, specially dyed particles, which not only emit fluorescence in the classification wavelength(s) or wavelength band(s) but also in the reporter wavelength or wavelength band, may be used in conjunction with the systems described herein.

The methods described herein generally include analyzing images of particles and processing data measured from the images to determine the location of the particles within the images. Subsequent processing of the one or more characteristics of the particles can be performed according to the methods described in U.S. Pat. No. 5,736,330 to Fulton, U.S. Pat. No. 5,981,180 to Chandler et al., U.S. Pat. No. 6,449,562 to Chandler et al., U.S. Pat. No. 6,524,793 to Chandler et al., U.S. Pat. No. 6,592,822 to Chandler, and U.S. Pat. No. 6,939,720 to Chandler et al. as well as U.S. patent application Ser. No. 11/534,166 to Roth et al. which are incorporated by reference as if fully set forth herein.

Turning now to the drawings, it is noted that FIG. 1 is not drawn to scale. In particular, the scale of some of the elements of the figure is greatly exaggerated to emphasize characteristics of the elements. Some elements of the system have not been included in the figures for the sake of clarity.

One embodiment of a system configured to generate, acquire, or supply images of particles and to process the images according to embodiments of methods described herein is shown in FIG. 1. The system shown in FIG. 1 may be used in applications such as multi-analyte measurement of particles. The system includes an imaging subsystem that includes light source 10. Light source 10 may include one or more light sources such as light emitting diodes (LED), lasers, arc lamps, incandescent lamps, or any other suitable light sources known in the art. In addition, or alternatively, the light source may include more than one light source (not shown), each of which is configured to generate light a different wavelength or a different wavelength band. One example of an appropriate combination of light sources for use in the system shown in FIG. 1 includes, but is not limited to, two or more LEDs. Light from more than one light source may be combined into a common illumination path by a beam splitter (not shown) or any other suitable optical element known in the art such that light from the light sources may be directed to the particles simultaneously. Alternatively, the imaging subsystem may include an optical element (not shown) such as a reflecting mirror and a device (not shown) configured to move the optical element into and out of the illumination path depending on which light source is used to illuminate the particles. In this manner, the light sources may be used to sequentially illuminate the particles with different wavelengths or wavelength bands of light. The light source(s) may also illuminate the substrate from above, rather than below the substrate (not shown).

The light source(s) may be selected to provide light at wavelength(s) or wavelength band(s) that will cause the particles or material coupled thereto to emit fluorescence. For instance, the wavelength(s) or wavelength band(s) may be selected to excite fluorescent dyes or other fluorescent materials incorporated into the particles and/or coupled to a surface of the particles. In this manner, the wavelength(s) or wavelength band(s) may be selected such that the particles emit fluorescence that is used for classification of the particles. In addition, the wavelength(s) or wavelength band(s) may be selected to excite fluorescent dyes or other fluorescent materials coupled to the particles via a reagent on the surface of the particles. As such, the wavelength(s) or wavelength band(s) may be selected such that the particles emit fluorescence that is used to detect and/or quantify reaction(s) that have taken place on the surface of the particles.

As shown in FIG. 1, the imaging subsystem may include optical element 12 that is configured to direct light from light source 10 to substrate 14 on which particles 16 are immobilized. In one example, optical element 12 may be a collimating lens. However, optical element 12 may include any other appropriate optical element that can be used to image light from light source 10 onto substrate 14. In addition, although the optical element is shown in FIG. 1 as a single optical element, it is to be understood that optical element 12 may include more than one refractive element. Furthermore, although optical element 12 is shown in FIG. 1 as a refractive optical element, it is to be understood that one or more reflective optical elements may be used (possibly in combination with one or more refractive optical elements) to image light from light source 10 onto substrate 14.

Particles 16 may include any of the particles described above. Substrate 14 may include any appropriate substrate known in the art. The particles immobilized on substrate 14 may be disposed in an imaging chamber (not shown) or any other device for maintaining a position of substrate 14 and particles 16 immobilized thereon with respect to the imaging subsystem. The device for maintaining a position of substrate 14 may also be configured to alter a position of the substrate (e.g., to focus the imaging subsystem onto the substrate) prior to imaging. Immobilization of the particles on the substrate may be performed using magnetic attraction, a vacuum filter plate, or any other appropriate method known in the art. Examples of methods and systems for positioning microspheres for imaging are illustrated in U.S. patent application Ser. No. 11/270,786 to Pempsell filed Nov. 9, 2005, which is incorporated by reference as if fully set forth herein. The particle immobilization method itself is not particularly important to the method and systems described herein. However, the particles are preferably immobilized such that the particles do not move perceptibly during the detector integration period, which may be multiple seconds long.

As shown in FIG. 1, the imaging subsystem may include optical element 18 and beam splitter 20. Optical element 18 is configured to focus light from substrate 14 and particles 16 immobilized thereon to beam splitter 20. Optical element 18 may be further configured as described above with respect to optical element 12. Beam splitter 20 may include any appropriate beam splitter known in the art. Beam splitter 20 may be configured to direct light from optical element 18 to different detectors based on the wavelength of the light. For example, light having a first wavelength or wavelength band may be transmitted by beam splitter 20, and light having a second wavelength or wavelength band different than the first may be reflected by beam splitter 20. The imaging subsystem may also include optical element 22 and detector 24. Light transmitted by beam splitter 20 may be directed to optical element 22. Optical element 22 is configured to focus the light transmitted by the beam splitter onto detector 24. The imaging subsystem may further include optical element 26 and detector 28. Light reflected by beam splitter 20 may be directed to optical element 26. Optical element 26 is configured to focus the light reflected by the beam splitter onto detector 28. Optical elements 22 and 26 may be configured as described above with respect to optical element 12.

Detectors 24 and 28 may include, for example, charge coupled device (CCD) detectors or any other suitable imaging detectors known in the art such as CMOS detectors, two-dimensional arrays of photosensitive elements, time delay integration (TDI) detectors, etc. In some embodiments, a detector such as a two-dimensional CCD imaging array may be used to acquire an image of substantially an entire substrate or of all particles immobilized on a substrate simultaneously. In this manner, all photons from the illuminated area of the substrate may be collected simultaneously thereby eliminating error due to a sampling aperture used in other currently available systems that include a photomultiplier tube (PMT) and scanning device. In addition, the number of detectors included in the system may be equal to the number of wavelengths or wavelength bands of interest such that each detector is used to generate images at one of the wavelengths or wavelength bands.

Each of the images generated by the detectors may be spectrally filtered using an optical bandpass element (not shown) or any other suitable optical element known in the art, which is disposed in the light path from the beam splitter to the detectors. A different filter "band" may be used for each captured image. The detection wavelength center and width for each wavelength or wavelength band at which an image is acquired may be matched to the fluorescent emission of interest, whether it is used for particle classification or the reporter signal. In this manner, the imaging subsystem of the system shown in FIG. 1 may be configured to generate multiple images at different wavelengths or wavelength bands simultaneously. Although the system shown in FIG. 1 includes two detectors, it is to be understood that the system may include more than two detectors (e.g., three detectors, four detectors, etc.). As described above, each of the detectors may be configured to generate images at different wavelengths or wavelength bands simultaneously and/or sequentially by including one or more optical elements for directing light at different wavelengths or wavelength bands to the different detectors simultaneously and/or sequentially.

In addition, although the system is shown in FIG. 1 to include multiple detectors, it is to be understood that the system may include a single detector. The single detector may be used to generate multiple images at multiple wavelengths or wavelength bands sequentially. For example, light of different wavelengths or wavelength bands may be directed to the substrate sequentially, and different images may be generated during illumination of the substrate with each of the different wavelengths or wavelength bands. In another example, different filters for selecting the wavelength or wavelength bands of light directed to the single detector may be altered (e.g., by moving the different filters into and out of the imaging path) to generate images at different wavelengths or wavelength bands sequentially.

The imaging subsystem shown in FIG. 1, therefore, is configured to generate a plurality or series of images representing the fluorescent emission of particles 16 at several wavelengths of interest. In addition, the system may be configured to supply a plurality or series of digital images representing the fluorescence emission of the particles to a processor (i.e., a processing engine). In one such example, the system may include processor 30. Processor 30 may be configured to acquire (e.g., receive) image data from detectors 24 and 28. For example, processor 30 may be coupled to detectors 24 and 28 in any suitable manner known in the art (e.g., via transmission media (not shown), each coupling one of the detectors to the processor, via one or more electronic components (not shown) such as analog-to-digital converters, each coupled between one of the detectors and the processor, etc.). Preferably, processor 30 is at least configured to process and analyze these images to determine one or more characteristics of particles 16 such as a classification of the particles and information about a reaction taken place on the surface of the particles. The one or more characteristics may be output by the processor in any suitable format such as a data array with an entry for fluorescent magnitude for each particle for each wavelength. Specifically, the processor may also (e.g. alternatively or additionally) be configured to perform one or more steps of the method embodiments described herein to process and analyze the images.

Processor 30 may be a processor such as those commonly included in a typical personal computer, mainframe computer system, workstation, etc. In general, the term "computer system" may be broadly defined to encompass any device having one or more processors, which executes instructions from a memory medium. The processor may be implemented using any other appropriate functional hardware. For example, the processor may include a digital signal processor (DSP) with a fixed program in firmware, a field programmable gate array (FPGA), or other programmable logic device (PLD) employing sequential logic "written" in a high level programming language such as very high speed integrated circuits (VHSIC) hardware description language (VHDL). In another example, program instructions (not shown) executable on processor 30 to perform one or more steps of the computer-implemented methods described herein may be coded in a high level language such as C#, with sections in C++ as appropriate, ActiveX controls, JavaBeans, Microsoft Foundation Classes ("MFC"), or other technologies or methodologies, as desired. The program instructions may be implemented in any of various ways, including procedure-based techniques, component-based techniques, and/or object-oriented techniques, among others.

Program instructions implementing methods such as those described herein may be transmitted over or stored on a storage medium. The storage medium may include but is not limited to a read-only memory, a random access memory, a magnetic or optical disk, or a magnetic tape. For each image, all located particles and the values and/or statistics determined for each identified particle may be stored in a memory medium within the storage medium. The image processing methods described herein may be performed using one or more algorithms. As described in more detail below, the algorithms may be complex and, therefore, may be best implemented through a computer (e.g., processing device). As such, the methods described herein and particularly in reference to FIG. 2 may be referred to as "computer-implemented methods" and, thus, the terms "method" and "computer-implements method" may be used interchangeably herein. It is noted that the computer-implemented methods and program instructions of the systems described herein may, in some cases, be configured to perform processes other than those associated with methods described herein and, therefore, the computer-implemented methods and program instructions of systems described herein are not necessarily limited to the depiction in the figures.

According to one embodiment, a computer-implemented method for image data processing includes one or more of the following steps (i.e., high level operations): determining locations of particles within a first image, calculating a transform parameter, and applying the transform parameter to the locations of the particles within a first image to determine movement locations of the particles within the second image. In some embodiments, these steps may be performed sequentially in the order listed above.

Figure 2:
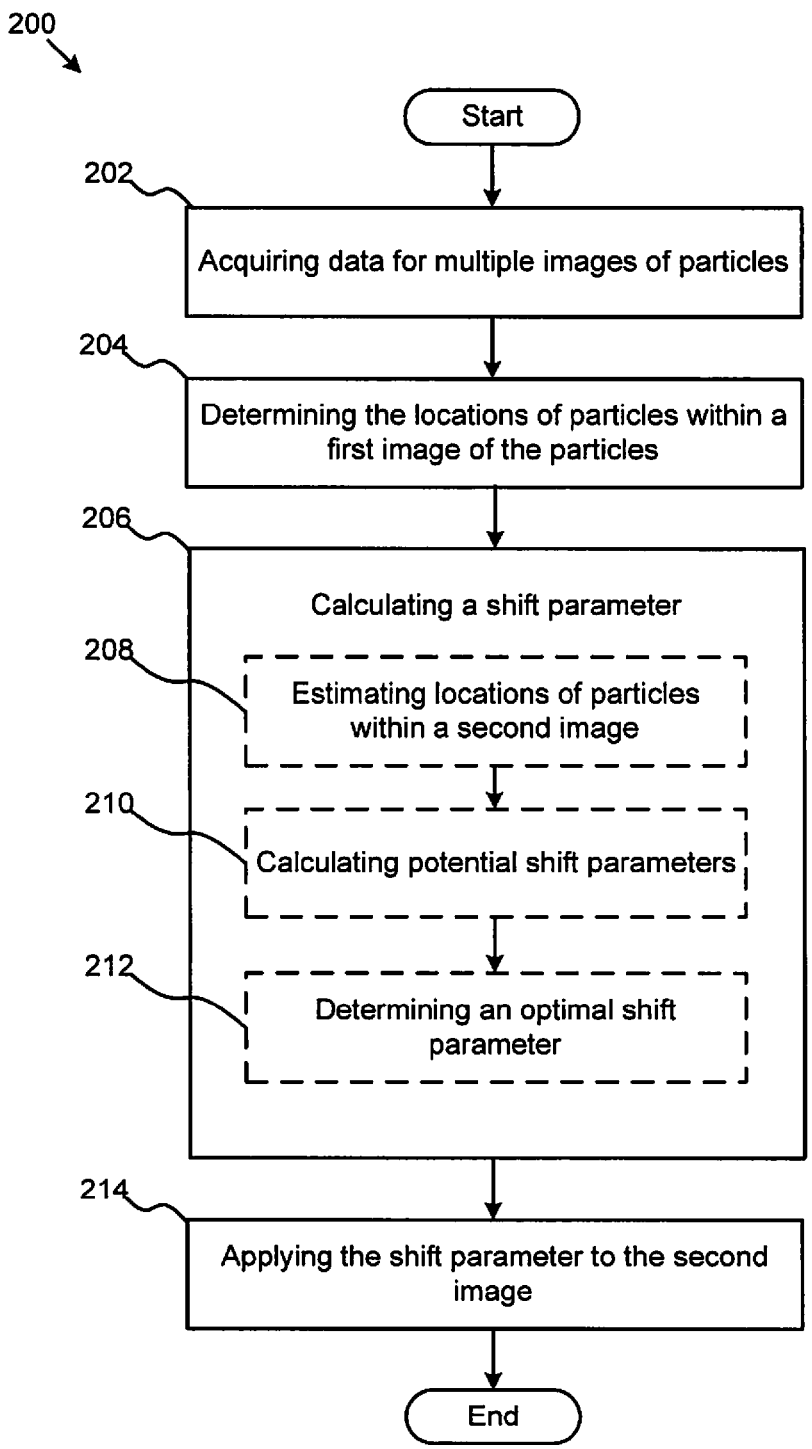
FIG. 2 is a flowchart outlining a method for processing images of particles.

FIG. 2 illustrates a method 200 illustrating an exemplary sequence of steps for image processing. As shown, the method 200 may include acquiring 202 data for multiple images of particles having fluorescence-material associated therewith, wherein each of the multiple images corresponds to a different wavelength band. In some cases, the data may be acquired directly from an imaging system, but in other cases, the data may be acquired from a storage medium. In either case, the data may be representative of multiple images taken at different wavelengths as noted above. Exemplary wavelengths that may be used may correspond to different color channels, such as but not limited to red for classification channel 1, red (e.g., a same or different wavelength of red) for classification channel 2, green for the reporter channel. As further noted above, in order to accommodate each color channel, the particles used for the method described herein may be specially dyed to emit at all wavelengths or in all wavelength bands of interest. In particular, in order to measure both classification and reporter signals within the multiple images, the methods described herein may be performed using specially dyed particles, which not only emit fluorescence in the classification wavelength(s) or wavelength band(s), but also in the reporter wavelength or wavelength band.

In some embodiments, an image taken a first bandwidth may be referred to as a "first image," and a subsequent/simultaneous image taken at the same or a different bandwidth may be referred to as a "second image." In preferred embodiments, the first image may be related to a classification channel (e.g., CL1 or CL2), and the second image may be related to a reporter channel (RP). As described above, the first image and the second image may be taken successively (in any order) or simultaneously.

In embodiments of the subsystem described with respect to FIG. 1, the particles, when viewed across one or more images, may appear to move. The movement of the particles between images may at least be caused by lens distortion and/or chromatic aberration. That is even though particles may not actually shift or move between multiple images they may appear to move based on lens distortion and or chromatic aberration. With respect to FIG. 1, the lens distortion and/or chromatic aberration may be a result of the filters (e.g., a filter wheel), light source 10, and/or one or more of optical elements 12, 18, 22 and 26. FIGS. 3A, 3B, and 3C demonstrate a movement that may be caused by grid distortion. FIG. 3A illustrates the grid distortion in a classification channel image (e.g., a first image) due to the lens distortion. As shown in the figure, the maximum distortion in the image occurs at the corners. FIG. 3B illustrates the grid distortion in a reporter channel image (e.g., a second image). As shown in this figure, the maximum distortion in the image also occurs at the corners. FIG. 3C illustrates an overlay of one corner of the reporter channel image and the classification channel image. As shown, the FIG. 3C illustrates a apparent movement towards the center of the images from the classification channel image to the reporter channel image. Thus, as a result of the lens distortion and chromatic aberration, a particle may appear to move between the classification channel image and the reporter channel image. As shown in FIG. 3, the lens distortion is a contributor to the radial movement. Light passing through any glass (e.g., optical elements, the chamber, and the like) may refract different wavelengths differently—like a prism. Variations on the chamber (e.g., the top plate) or other optical elements may cause chromatic aberration to vary as well.

After acquiring 202 data for multiple (e.g., at least two) images, the method 200 may proceed by determining the locations of particles within a first image of the particles. As discussed throughout, the particles may have florescence-material associated therewith. Moreover, in embodiments, the "first image" may refer specifically to a classification channel image. One of skill in the art will recognize a variety of image processing techniques to determine locations of particles within a classification channel image including peak searching and similar methods. For example, a variety of methods are discussed in U.S. patent application Ser. No. 11/534,166 to Roth et al.

In some embodiments, determining the location of particles within a classification channel image may be easier than determining the location of particles within a reporter channel image. As described above, the classification channel image may be configured to illuminate the particles themselves while the reporter channel image may be configured to illuminate the substances (e.g., analyte) bound to the particle. As such, a peak search (or similar algorithm) in a classification channel image may closely reveal the location of a particle. At the same time, a peak search (or similar algorithm) may reveal the location of the analyte—which may or may not correlate to the location of the particle. Rather, in some instances, such an algorithm may reveal the location of the analyte on the edge of the particle or even a different particle.

In some embodiments of the method 200, the method may include calculating 206 a transform parameter. A transform parameter defines an estimated movement in the locations of particles between the first image of the particles and the second image of the particles. Using the transform parameter would allow one to determine the location of particles in the second image as a function of the location of the particles in the first image.

Figure 4:
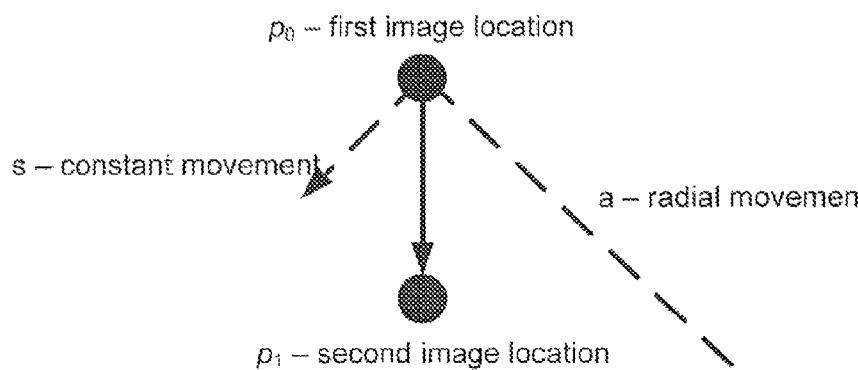
FIG. 4 illustrates a free body diagram of a particle.

In certain embodiments, the transform parameter may include a radial component and a constant component. For example, FIG. 4 illustrates one embodiment of a radial movement and a constant movement that may be used to define the transform parameter. The constant movement may be induced by the optical effects of the filter wheel. As shown in FIG. 4, $p_0$ illustrates the location of a particle in the first image, and similarly $p_1$ illustrates the location of the particle in the second image. The movement can be defined as the combination of two components: (1) s the vector of the constant movement, and (2) a the radial movement. The radial component may be proportional to the distance between the location of particles within the first image and a center O of the image. As such, the location of p1 may be determined using Equation 1:

$$p_1 = T(p_0) = p_0 + s + a(O - p_0) \qquad (1)$$

Using Equation 1 and the transform parameter (e.g., as defined by a and s), the location of particle in the first image may be determined. As defined above, Equation 1 (using components a and s) reflects a specific embodiment of the disclosed method. A transform parameter may include only a single component or even multiple components. The relationship between $p_0$ and $p_1$ need not be linear, and may even be non-linear.

In some embodiments, calculating 206 a transform parameter may include estimating 208 estimated locations of particles within a second image. As described above, an algorithm such a peak search algorithm may or may not find the location of particle in the second image. Such an algorithm may be used to estimate the locations of particles within a second image. Another method, referred to as the "maximal integral location" is discussed in more detail below.

Based on one or more of these estimated locations, potential transform parameters may be calculated 210. For example, a single pair of points (e.g., $p_0$ and an estimated $p_1$) may be used to define one or more potential transform parameters. In an embodiment of a transform parameter comprising more than one component, however, may require more than one pairs of points to determine a potential transform parameter. More than one pairs of points may be used to define a set of potential transform parameters—where each pair may define a single potential transform parameter. In some embodiments, by analyzing the set of potential transform parameters, an optimal transform parameter may be determined 212. In a simple embodiment, determining an optimal transform parameter may include taking the average, mean, mode, or the like of the set of potential transform parameters. Another method, using a Hough transform is described in more detail below.

Figure 5A:
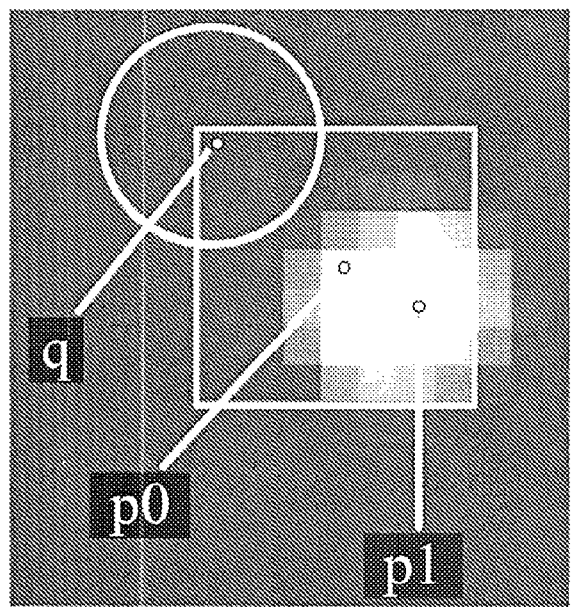
FIGS. 5A-5B illustrate a specific embodiment of determining a maximal integral location.

In some embodiments, estimating 208 the locations of particles within the second image may include determining the maximal integral location based on the second image and the locations of the particles within the first image. FIG. 5A illustrates one embodiment of finding the maximal integral location (e.g., an estimated $p_1$). Finding the maximal integral location includes estimating the location of $p_1$ in the second image based the location of $p_0$ in the first image. In some embodiments, finding the maximal integral location includes finding the location of the point $p_0$ in the second image. The original location of the particle $p_0$ is illustrated in FIG. 5A. Finding the maximal integral location may further include analyzing the image a certain distance around $p_0$. This certain distance around $p_0$ may define an area to be analyzed. In FIG. 5A, the part of the image contained within the square may be analyzed. More specifically, in the figure, the square is defined by the three pixels in each direction from $p_0$. In various embodiments this distance may be any number of pixels or other metric. In some embodiments, the certain distance around $p_0$ may be defined by as a circle (e.g., based on a radius) around $p_0$ instead.

Finding the maximal integral location may further include for one or more points q in the area to compute the integrated intensity centered at q. As shown in the figure, the set of pixels in the areas to be analyzed (e.g., the square box) may define a set of points q. For each point g, the integrated intensity is computed. In the specific embodiment of the figure, the area to be integrated is defined by the circle (e.g., with a radius of 2.5 pixels). In other embodiments, the area to be integrated may be defined by a square (e.g., with a half side length of 2.5 pixels). In some embodiments, the value of q that maximizes the integral intensity is estimated to be the location of the particle at in the second image (e.g., $p_1$).

Figure 5B:
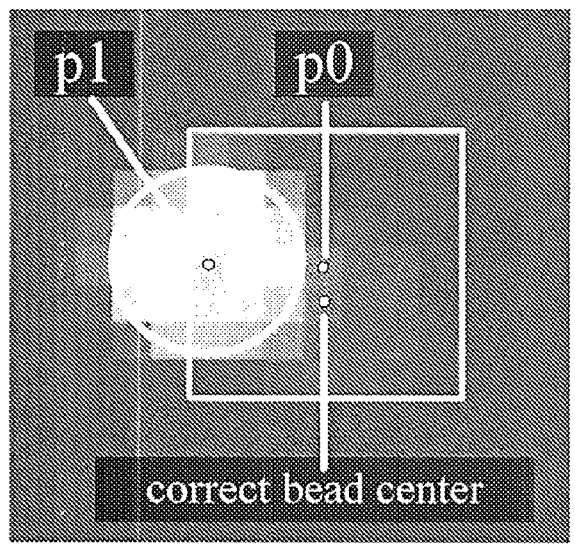

As shown in FIG. 5A, in this specific embodiment, the maximal integral location method correctly identifies the location of the particle in the second image (e.g., $p_1$). In contrast, in FIG. 5B, the maximal integral location method does not correctly identify the location of the particle in the second image. In this figure, there is both a "dim" particle and a "bright" particle in the second image. Given the location $p_0$ of the dim particle in the first image, the actual location of the particle in the second image is identified "correct bead center" in the figure. However, due to interference from the adjacent particle, the point $p_1$ is found as the maximal integral location. The estimated location of the particle shown is FIG. 5(b) is an outlier. Whereas the pair of points ($p_0$ and $p_1$) from FIG. 5A may be used to calculate a "correct" transform parameter, the pair of points from FIG. 5B may result in an "incorrect" transform parameter.

The method steps discussed with respect to FIG. 5 are explained in a specific embodiment with respect to Equations 2 and 3. Equation 2 defines f(p) the sum of pixels in the second image (e.g., RP) about point p with integration radius r. Equation 3 defines $K(p_0, m)$ as the set of integrated intensities in the second image (e.g., RP) at all points $p_1$ less than m distance from $p_0$.

$$f(p) = \Sigma_{\{q_1 \| q - p \| < r\}} RP(q) \qquad (2)$$

$$K(p_o, m) = \{f(p_1) : \forall p_1; \|p_1 - p_0\| < m\} \qquad (3)$$

Given the center of a particle $p_0$ in the first image, the maximal integral location of this particle in the second image may be defined (in this specific embodiment) as the location $p_1$ where $f(p_1)$ is the maximum of $K(p_0, m)$. Here, m is the maximum detectable movement of a particle from the first image to the second image.

After estimating 208 the locations of particles within a second image, a set of potential transform parameters may be calculated, and this set of transform parameters may be used to determine an optimal transform parameter. As discussed with respect to FIG. 5, some of the pairs of points (e.g., $p_0$ and the estimated $p_1$) may be "correct." That is the estimated $p_1$ corresponds to the actual location of the particle in the second image. Likewise, some of the pairs of points will be "incorrect." Since many of the pairs of points will be right (e.g., in the set of all pairs it is more likely than not that $p_1$ was estimated correctly), an analysis of the set can reveal an optimal transform parameter.

In a specific embodiment, potential transform parameters may be calculated based on each pair of points. Further, a transform may be used (e.g., a Hough transform) where each pair of points "votes" for potential transform parameters. Thus, the optimal transform parameter would be the potential transform parameter that gets the most overall votes. Alternative algorithms that may be used include 1) a random sample consensus (RANSAC) of $p_0$, $p_1$ pairs and 2) an elimination of variables by first specifically choosing $p_0$, $p_1$ close to O to eliminate the effect of a, solving for s, and then using both s and the remaining p0,p1 pairs to solve for a.

A specific embodiment of 210 calculating potential transform parameters and determining 212 an optimal transform parameter is described below with respect to Equations 4 and 5. This embodiment uses a transform parameters with a radial and constant component as defined by Equation 1. Equation 4 solves Equation 1 for s, and Equation 5 solves Equation 1 for a.

$$s = p_1 - p_0 - a(O - p_0) \tag{4}$$

$$a = \frac{(o - p_0)^T (p_1 - p_0 - s)}{\|O - p_0\|^2} \tag{5}$$

The pseudo code below introduces a parameter V (e.g., a Hough space or a vote space).

1) Initialize the array V to 0
2) For each value a in A do
    For each pair p0, p1 do
        Compute s(p0, p1, a)
        Coerce s to closest quantized value s' in S
        Increment V[s'] [a]
3) For each value s in S do
    For each pair p0, p1 do
        Compute a(p0, p1, s)
        Coerce a to closest quantized value a' in A
        Increment V[s] [a']

In a specific embodiment, vectors may vary in the set of S. For example, the set S may be defined to vary from <−3,−3> to <3,3>, and S may quantized at every ⅕ pixel. Such a set of S will yield 30 possible variations. One of skill in the art will recognize that the set S may be defined to be larger or smaller either by increasing/decreasing the range of S or changing the quantization factor. The scalar a may vary in the set of A. For example, the set A may be defined to vary from −0.0004 to 0.0004 and quantized at every 0.0001 steps. Such a set of A has a size of 80. In embodiments where an image has 2048× 2048 pixels, every 0.001 change in a corresponds to roughly 1 pixel of radial movement at the image boundary (since the distance from O to the edge of the image is 1024 pixels). A range of −0.004 to 0.004 could enable the detection of approximately 4 pixels of radial movement. One of skill in the art will recognize that the set A may be changed by changing the range of quantization. Increasing the range of either S or A could result in detecting larger components of radial and scalar movement. Moreover, using a finer quantization could result in a finer determinations of an optimal transform parameter.

FIG. 6 illustrates a particular example of portions of array V. Since s is a two-dimensional vector, it is represented on the x and y axis. As shown, S varies from −3 to 3 along both axes. The component a is represented on the z axis (vertically), and A varies from −0.004 to 0.004. Each of the FIGS. 6A, 6B, 6C, and 6D represent a slice of array V. As shown, FIG. 6C represents the highest peak in the vote space. This peak occurs at quantized location a=0.0009, s=<−0.4, 0.4>. The quantized location, however, may not be the "optimal transform parameter." In some embodiments, computing the center of mass inside a volume of vote space about the peak location yields the optimal transform parameter: a*=9.07×10$^{-4}$ and s*=<−0.3684, 0.3800>.

In some embodiments, the method 200 may further include applying 214 the transform parameter to the second image. In such an embodiment, the calculated transform parameter (e.g., the optimal transform parameter) may be used to determine the location of the particles in the second image based on the location of the particles in the first image. Using Equation 1 for example, the optimal transform parameter values a and s may be used to determine the movement of each of the particles.

In some embodiments, prior to applying 214 the transform parameter to the second image, an error vector may be calculated. Thus, the error vector may be account for at least one source of error in the calculation of the transform parameter. Specifically, the error vector may take into account the affect of neighboring particles. Moreover, neighboring particles may apply a force on a given particle causing them to move with respect to time. The error vector is defined in Equation 6.

$$\epsilon = p_1 - T(p_0; a^*; s^*) = p_1 - p_0 - s^* - a^*(O - p_0) \tag{6}$$

Figure 7:
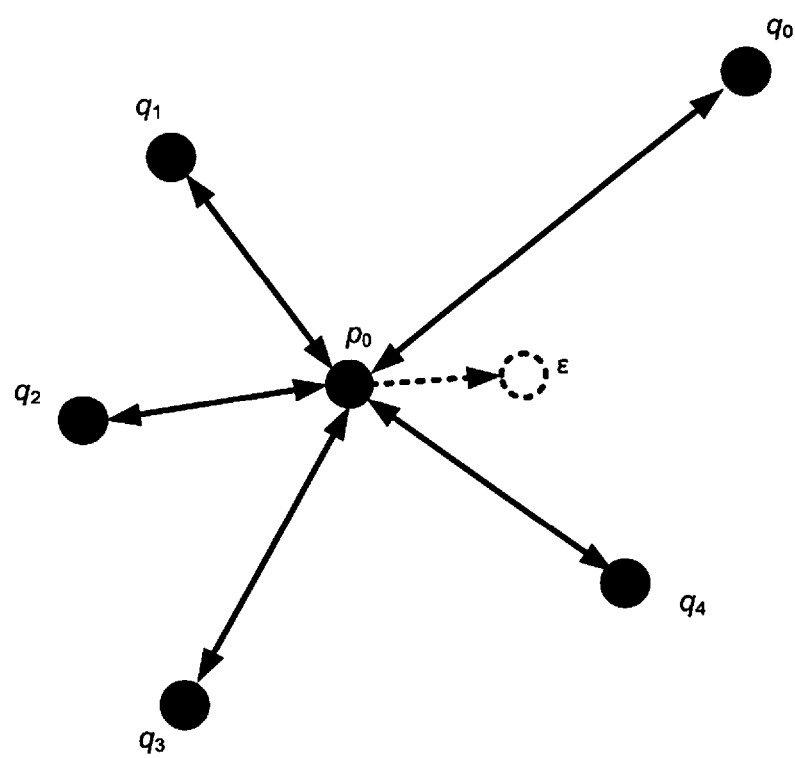
FIG. 7 illustrates an additional free body diagram of a particle.

As illustrated in FIG. 7, each particle q may exert a force on $p_0$. More specifically, this force may include a magnetic force between the particles. The force exerted by a particle q may have a direction as defined by Equation 7, and the force exerted by a particle q may have a magnitude as defined by Equation 8. The magnitude of the force exerted by a particle q is inversely proportional to the square of the distance from q to $p_0$. In addition to calculating the square of the distance between q and $p_0$, Equation 8 introduces a variable g. The total error vector combining the forces exerted on $p_0$ by all neighboring beads q is summed together in Equation 9.

$$\text{Direction} = \pm (q - p_0) \tag{7}$$

$$\text{Magnitude} = \frac{g}{\|q - p_0\|^2} \tag{8}$$

$$\varepsilon = g \Sigma_{q \in Q} \frac{(q - p_0)}{\|q - p_0\|^3} \tag{9}$$

Once an optimal value of g has been found, Equation 1 can be modified to account for the error vector. Equation 10 below accounts for the radial component, the constant component, and the error component:

$$p_1 = T(p_0) = p_0 + s + a(O - p_0) + g \Sigma_{q \in Q} \frac{(q - p_0)}{\|q - p_0\|^3} \tag{10}$$

Similar to the calculation of the optimal transform parameter, the error component can be determined by estimating a set of potential values for the error component and calculating the optimal value of the error component. Equation 11 illustrates how to calculate g based on a given point p surrounded by particles q within a given radius to form the set Q $$\text{Letting } W = \Sigma_{q \in Q} \frac{(q - p_0)}{\|q - p_0\|^3} : \tag{11}$$

$$g = \frac{w^T s}{\|w\|^2}$$

An optimal value of g can be calculated using the following pseudo code:

```
1) For each p0,p1 pair do
     Compute ε
     Define Q to be neighboring particles "close" to p0
     Compute W
     Compute g
     If g is within a specified bounds (e.g., –20 to 0), record in
G
     Select the optimal value g* from G
```

As discussed above, the optimal values of a, s, and g may then be used to determine the movement of particles between a first image and a second image.

It will be appreciated to those skilled in the art having the benefit of this disclosure that this invention is believed to provide computer-implemented methods, storage mediums, and systems for image data processing. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An apparatus, comprising:
   at least one processor; and
   an imaging subsystem configured to accept a sample that includes a plurality of discrete components, and capture images of the plurality of discrete components, wherein the plurality of discrete components have fluorescence material associated therewith;
   wherein the at least one processor is configured to:
      determine locations of selected ones of the plurality of discrete components within a first image of the captured images;
      calculate a transform that includes a radial component and a constant component, the radial component being proportional to a distance between the locations of the selected ones within the first image and a center of the first image; and
      determine estimated locations of the selected ones within a second image of the captured images by applying the transform to the locations of the selected ones within the first image.

2. The apparatus of claim 1, wherein the plurality of discrete components includes at least one of the following types of component: a microparticle, a nanoparticle, a quantum dot, or a cell.

3. The apparatus of claim 2, wherein the microparticle is a polystyrene bead or a latex bead.

4. The apparatus of claim 1, wherein the fluorescence material is a fluorescent dye.

5. The apparatus of claim 1, wherein the at least one processor is further configured to:
   determine potential locations of the selected ones within the second image by measuring maximal integral locations within the second image; and
   calculate the transform based on the determined potential locations.

6. The apparatus of claim 5, wherein the determined potential locations are based on locations within the second image that correspond to the locations of the selected ones within the first image.

7. The apparatus of claim 1, wherein the at least one processor is further configured to determine an error vector based on proximities between individual pairs of the selected ones.

8. A method, comprising:
   a computing system analyzing a first image of particles having fluorescence material associated therewith to determine locations of the particles within the first image; and
   the computing system estimating locations of the particles within a second image, wherein the estimating includes:
      applying a transform to the locations of the particles within the first image to determine estimated locations of the particles within the second image, wherein the transform includes a radial component and a constant component, the radial component being based on a distance between the locations of the particles within the first image and a center of the first image.

9. The method of claim 8, wherein the transform is determined based on a plurality of potential transforms, each potential transform being based on a subset of the particles.

10. The method of claim 9, wherein the transform is determined via a Hough transform based on the plurality of potential transforms.

11. The method of claim 8, wherein the particles have at least a first fluorescence material and a second, different fluorescence material associated therewith.

12. The method of claim 11, wherein the first fluorescence material is a classification material operable to indicate the particles.

13. The method of claim 12, wherein the second fluorescence material is a reporter material operable to indicate an analyte associated with the particles.

14. The method of claim 8, wherein the transform is further based at least in part on measured maximal integral locations of particles in the second image.

15. The method of claim 8, wherein the transform is further based at least in part on a selected subset of particles within a determined radius of the center of the first image.

16. The method of claim 8, wherein the particles include at least one of the following types of particles: a microparticle, a nanoparticle, a quantum dot, or a cell.

17. The method of claim 16, wherein the microparticle is a polystyrene bead or a latex bead.

18. The method of claim 8, wherein the fluorescence material is a fluorescent dye.

19. A non-transitory, computer-readable medium having instructions stored thereon that, in response to execution by a computing system, cause the computing system to carry out operations comprising:
   receiving data indicative of locations of particles within a first image, wherein the particles have fluorescence material associated therewith; and determining estimated locations of the particles within a second image by applying a transform to the locations of the particles within the first image, wherein the transform includes a radial component and a constant component, the radial component being proportional to a distance between the locations of the particles within the first image and a center of the first image.

20. The medium of claim 19, wherein the radial component corresponds to optical distortion caused by chromatic aberration.

21. The medium of claim 19, wherein the constant component corresponds to optical distortion caused by an optical filter wheel.

22. The medium of claim 19, wherein the fluorescence material is attached to the particles.

23. The medium of claim 19, wherein the particles are microbeads.

24. The medium of claim 19, wherein the transform is selected as an optimal transform based on a plurality of potential transforms.

* * * * *